United States Patent
Laugharn, Jr.

(10) Patent No.: US 9,267,867 B2
(45) Date of Patent: *Feb. 23, 2016

(54) METHOD AND APPARATUS FOR TREATMENT ENHANCEMENT IN ACOUSTIC PROCESSING OF SAMPLES

(75) Inventor: James A. Laugharn, Jr., Winchester, MA (US)

(73) Assignee: Covaris, Inc., Woburn, MA (US)

( * ) Notice: Subject to any disclaimer, the term of this patent is extended or adjusted under 35 U.S.C. 154(b) by 1365 days.

This patent is subject to a terminal disclaimer.

(21) Appl. No.: 12/489,693

(22) Filed: Jun. 23, 2009

(65) Prior Publication Data

US 2009/0317884 A1 Dec. 24, 2009

Related U.S. Application Data (60) Provisional application No. 61/075,137, filed on Jun. 24, 2008.

(51) Int. Cl.
| | | |
|---|---|---|
| C12M 1/33 | (2006.01) | |
| C12M 3/06 | (2006.01) | |
| G01N 1/28 | (2006.01) | |
| B01F 11/02 | (2006.01) | |
| G01N 35/00 | (2006.01) | |

(52) U.S. Cl.
CPC ............ *G01N 1/286* (2013.01); *B01F 11/0283* (2013.01); *B01J 2219/0074* (2013.01); *B01J 2219/00308* (2013.01); *B01J 2219/00344* (2013.01); *B01J 2219/00486* (2013.01); *B01J 2219/00722* (2013.01); *G01N 2035/00554* (2013.01)

(58) Field of Classification Search
CPC .................. B01F 11/0283; B01J 2219/00308; B01J 2219/00344; B01J 2219/00722; B01J 2219/0074; B01J 2219/00486; G01N 2035/00554

USPC .............. 435/173.7, 306.1; 261/94; 366/116, 366/127; 422/128; 516/58

See application file for complete search history.

(56) References Cited

U.S. PATENT DOCUMENTS

| | | | | |
|---|---|---|---|---|
| 4,930,532 A | * | 6/1990 | Mayer ........................... | 134/184 |
| 6,515,030 B1 | * | 2/2003 | Bechtel et al. .................. | 516/58 |
| 7,147,692 B2 | * | 12/2006 | Fornai et al. .................... | 95/210 |
| 2002/0009015 A1 | | 1/2002 | Laugharn et al. | |
| 2008/0031094 A1 | * | 2/2008 | Laugharn et al. ............. | 367/138 |

FOREIGN PATENT DOCUMENTS

| | | | |
|---|---|---|---|
| GB | | 2308182 A | 6/1997 |
| WO | WO 2008/016691 A2 | | 2/2008 |

OTHER PUBLICATIONS

International Search Report for International Application No. PCT/US2009/003719 mailed Oct. 23, 2009.
Written Opinion of the International Searching Authority for International Application No. PCT/US2009/003719 mailed Oct. 23, 2009.

* cited by examiner

*Primary Examiner* — Michael Hobbs
(74) *Attorney, Agent, or Firm* — Wolf, Greenfield & Sacks, P.C.

(57) ABSTRACT

Method and apparatus for controlling acoustic treatment of a sample including a liquid. A processing volume in which the sample is acoustically treated may be controlled, e.g., by positioning a suitable element so as to reduce and/or eliminate a headspace at a sample/gas interface. An interaction between the acoustic energy and the sample may be controlled, e.g., by using an energy director positioned at least partially in the sample that helps to reduce splashing or other sample ejection that would otherwise occur.

17 Claims, 5 Drawing Sheets

METHOD AND APPARATUS FOR TREATMENT ENHANCEMENT IN ACOUSTIC PROCESSING OF SAMPLES

BACKGROUND

1. Field of the Invention

Systems and methods for processing of samples with acoustic energy are generally disclosed.

2. Related Art

Acoustic energy-based sample processing devices, such as Adaptive Focused Acoustic apparatuses made by Covaris of Woburn, Mass., are effective for homogenization and disruption of biological tissues, cells and other sample material. With such devices, a controlled acoustic field enables repeatable processes to be developed which often result in higher recovery of target molecules. Such target molecules may be, for example, DNA, RNA, proteins, and the like. Target molecules or other materials may be contained as samples within a vessel.

SUMMARY OF INVENTION

In some cases, acoustic treatment of a sample causes cavitation or other disruption in the sample such that some of the sample splashes or is otherwise ejected from the main sample volume. Some of the ejected sample portions may fall back into the main sample volume, but other sample portions may adhere to the vessel walls above the main sample volume or be ejected from the vessel entirely. One solution for this problem is to reduce the acoustic energy used to treat the sample, but may result in slower and/or incomplete processing of the sample.

The inventor has appreciated that for some applications, it is useful to process samples in vessels with acoustic energy such that the samples do not splash or otherwise move into a region in the vessel, or out of the vessel entirely, where acoustic processing is unable to occur and thus sample material is wasted. In different aspects presented herein, a volume control member, an energy director, or a combination thereof may be used to reduce splashing or ejection of a portion of the sample from an interface between the sample and a headspace (gas region) above the sample. More specifically, an energy director may serve to assist in controlling the interaction of the sample and the directed acoustic energy so as to mitigate excessive mixing, which may cause splashing or ejection of the sample from the interface between the sample and the headspace above the sample. A volume control member may assist in limiting the volume of headspace above a sample contained within a vessel so as to substantially prevent sample material from traveling significant distances from the interface. "Mixing" is used herein to refer to a variety of different levels of doing work on the sample or otherwise moving sample material without physically contacting the material, including lysing (such as cell lysis), extraction, permeabilizing, stirring, catalyzing, degrading, fluidization, heating, particle breakdown, DNA shearing, or disruption of molecular bonds in the sample. In some embodiments, the acoustic energy has a frequency of between about 100 kilohertz and about 100 megahertz and a focal zone with a width of less than about 2 centimeters that is applied to the sample.

In one aspect of the invention, an acoustic treatment device includes a vessel arranged to hold a sample including a liquid, and an acoustic energy source that is separated from the vessel and provides acoustic energy to the sample in the vessel. A vessel holder may support the vessel so that the vessel is at a location at least partially in a focal zone of the acoustic energy, and an energy director may be positioned at least partially in the sample to control interaction between the acoustic energy and the sample so as to reduce mixing in a portion of the sample that would occur in the absence of the energy director. For example, the energy director may act as a nucleation site for cavitation in the liquid when the sample is subjected to the acoustic energy. As a result, cavitation may occur local to the surface of the energy director such that shear forces resulting from the cavitation are directed onto a surface of the energy director. This arrangement may allow the energy director to absorb some of the energy caused by cavitation, and thus reduce splashing or other unwanted sample movement due to excessive mixing. In addition, the energy director-mediated mixing at the energy director surface may assist in causing desired interaction between the acoustic energy and the sample. For example, in some embodiments, placing an energy director including a polymer material with exposed pore sizes of about 10-200 microns in a sample has been found especially useful in certain DNA shearing operations, allowing DNA to be sheared into a population of DNA fragments having a relatively uniform base pair length, such as about 3000 base pairs. The energy director may take one of several different forms, including a porous hydrophobic element (e.g., a plug), a plurality of beads (which may be positively, negatively or neutrally buoyant in the sample), or a rod-shaped element (such as a 1-2 mm diameter, 1-2 cm long glass or polymer cylinder) that is placed in the sample and within the acoustic energy focal zone.

In another embodiment, a volume control member may be used to define a headspace in the vessel above the sample. In some arrangements, the volume control member may be located at, below or above a top of the sample, i.e., the interface between the sample liquid and air or other gas. The volume control member may help define a processing volume where the sample, or portions of the sample are exposed to acoustic energy and/or other processing conditions. In some cases, the volume control member and energy director may be formed as part of the same element. For example, a plug may depend from a cap on the vessel and have a lower end located below the sample/gas interface. The lower end may not only reduce the headspace in the vessel, but also function as an energy director. The volume control member may be arranged to permit a pressure local to the sample in the vessel to equalize with an ambient pressure outside of the vessel. For example, the volume control member may include a valve, a gas permeable membrane, a porous material, a filter, sponge, and/or an orifice, for allowing gas to pass through at least a portion of the volume control member.

In another aspect of the invention, a method for processing a sample includes providing a sample in a vessel, subjecting the sample to acoustic energy sufficient to cause mixing in a liquid material of the sample, and providing an energy director at least partially in the sample to control interaction between acoustic energy and the sample so as to reduce mixing in a portion of the sample that would occur in the absence of the energy director. In some embodiments, the acoustic energy may be sufficient to cause at least one of lysing, extraction, permeabilizing, stirring, catalyzing, degrading, fluidization, heating, particle breakdown, DNA shearing or disruption of molecular bonds in the sample. In one specific embodiment, DNA shearing may be accomplished by using an energy director and a vessel made of a hydrophobic material, e.g., to shear DNA fragments in the sample from relatively large sizes (10 kbp in length and up) into shorter fragments (e.g., about 3 kbp in length). For example, using an energy director in the form of a hydrophobic polymer material having exposed pores of about 100 microns in diameter has been found effective in causing DNA shearing that results in most of the DNA fragments in a sample to have a size of about 3 kbp. Use of a hydrophilic energy director and vessel has been found to be effective in shearing DNA to sizes smaller than about 3 kbp.

In another aspect of the invention, an acoustic treatment device includes a vessel arranged to hold a sample that includes a liquid, a cap arranged to engage with the vessel and cover the vessel opening, and an energy director positioned in the vessel to control interaction between acoustic energy and the sample. The energy director is arranged to control the acoustic energy/sample interaction where the acoustic energy has a frequency of between about 100 kilohertz and about 100 megahertz and a focal zone with a width of less than about 2 centimeters emitted remote from the vessel. In general, the energy director reduces mixing of the sample that would occur in the absence of the energy director, e.g., to reduce splashing and/or to facilitate certain actions such as shearing at or near the energy director surface. In one embodiment, the energy director is fixed to the cap and is positioned in the sample when the cap is engaged with the opening. As a result, the energy director may be properly positioned in the vessel by simply placing the cap on the vessel. Moreover, contact of the energy director with contaminants may be reduced since the energy director may be handled by grasping the cap only.

In one embodiment, the energy director and the vessel are made of a hydrophilic material, and the vessel and energy director are arranged to enhance shearing of DNA in the sample having a base pair length of about 3000 or less caused by the acoustic energy. In another embodiment the energy director and the vessel are made of a hydrophobic material, and the vessel and energy director are arranged to enhance shearing of DNA in the sample having a base pair length of about 3000 or more caused by the acoustic energy.

Other advantages and novel features of the invention will become apparent from the following detailed description of various non-limiting embodiments when considered in conjunction with the accompanying figures and claims.

BRIEF DESCRIPTION OF THE DRAWINGS

Aspects of the invention are described with reference to the following drawings in which numerals reference like elements, and wherein.

DETAILED DESCRIPTION

Aspects of the invention are not limited in application to the details of construction and the arrangement of components set forth in the following description or illustrated in the drawings. Other embodiments may be employed and aspects of the inventions may be practiced or be carried out in various ways. Also, the phraseology and terminology used herein is for the purpose of description and should not be regarded as limiting.

As described above, acoustic treatment systems can be useful for the homogenization and disruption of biological tissues, cells and other sample material, with the end goal of recovering target molecules from the sample material, such as DNA, RNA, proteins, and the like. In addition, such systems may be used along with aspects of the invention for DNA shearing, e.g., to reduce the base pair length of DNA fragments from 1,000s or 10,000s of base pairs to lengths of 3 k base pairs or smaller. Examples of such acoustic treatment systems and control arrangements are described in U.S. Pat. Nos. 6,948,843 and 6,719,449, assigned to Covaris of Woburn, Mass.

Although acoustic-based sample disruption processes such as those performed using Covaris Adaptive Focused Acoustic systems are very efficient, they sometimes require that an operator define general treatment parameters before processing samples. For example, one common objective is to enable a sample to spend as much time in a focal zone of the acoustic field as possible, which may allow DNA, proteins or other materials in the sample to be more fully extracted. Typically, achieving this result requires that the acoustic energy at the focal zone be essentially throttled down (e.g., by reduced intensity, duty cycle, and/or duration) to keep a pre-homogenized sample from splashing or otherwise moving out of the acoustic focal zone. For example, if a 1 gram muscle sample is loaded into a 10 ml tube with 2 ml of distilled water, there will be essentially 7 ml of headspace between the top surface of the sample (including the liquid and muscle material) and the top of the tube. If the acoustic energy applied to the sample is at a sufficiently high intensity, the sample/air interface in the tube may be readily broken. This may result in particles of the muscle material being splashed up and out of the focal zone. These particles may adhere to the interior wall of the tube relatively far removed from the focal zone, possibly even as far away as a cap on the tube. A sample particle which is adhered to the tube wall or cap likely will not be homogenized or otherwise acoustically treated and the resultant homogenate may be incomplete and variable. To prevent this problem, what is typically done is to reduce the acoustic dose so the sample material is not ejected from the acoustic focal zone, and instead spends as much time as possible in the acoustic focal zone during a process.

In accordance with one aspect of the invention, a retention time of a sample in an acoustic focal zone may be increased, e.g., by minimizing the gaseous headspace in a processing vessel and/or controlling interaction between the sample and acoustic energy, thereby enabling higher acoustic doses to be delivered to the sample. As a result, sample processing time may be reduced, improving processing efficiency and target recovery.

In some embodiments, interaction between the sample and acoustic energy may be controlled, e.g., by an energy director element positioned at least partially in the sample. The energy director may absorb or otherwise direct acoustic energy such that the sample is not disrupted in a way that results in splashing or other ejection of material at the interface between the sample and a gas (e.g., the top surface of the sample in a vessel). The energy director may be a polymer, glass, metal or other component that is placed (e.g., loose and not connected to the vessel) in the sample. In some arrangements, the energy director may function as a nucleation site for cavitation and cause shear forces created during collapse to be directed to the surface of the energy director, instead of to portions of the sample. Thus, the sample may experience less shear stress during acoustic processing. This type of arrangement has been found to be particularly useful in DNA shearing applications. The energy director may also function as a thermal energy emitter, if desired, e.g., the energy director may be heated by acoustic energy and release heat to surrounding sample material, to the vessel, to the cap and/or to other components.

Figure 1:
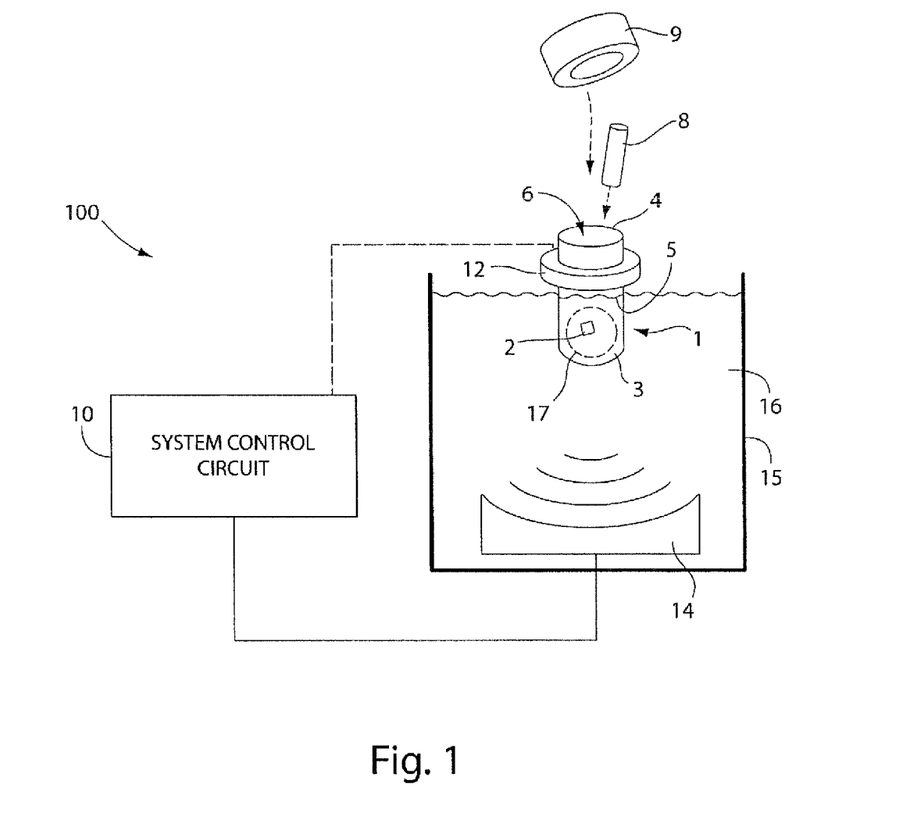
FIG. 1 shows a schematic block diagram of an acoustic treatment system that incorporates one or more aspects of the invention.

FIG. 1 shows a schematic block diagram of an acoustic treatment system 100 that incorporates one or more aspects of the invention, including an energy director that is associated with a sample. It should be understood that although embodiments described herein may include most or all aspects of the invention, aspects of the invention may be used alone or in any suitable combination with other aspects of the invention. In this illustrative embodiment, the acoustic treatment system 100 includes an acoustic transducer 14 (e.g., including one or more piezoelectric elements) that is capable of generating an acoustic field (e.g., at a focal zone 17) suitable to cause mixing, e.g., caused by cavitation, and/or other affects in a sample 1 contained in a vessel 4. The acoustic transducer 14 may produce acoustic energy within a frequency range of between about 100 kilohertz and about 100 megahertz such that the focal zone 17 has a width of about 2 centimeters or less. The focal zone 17 of the acoustic energy may be any suitable shape, such as spherical, ellipsoidal, rod-shaped, or column-shaped, for example, and be positioned at the sample 1. The focal zone 17 may be larger than the sample volume, or may be smaller than the sample volume, as shown in FIG. 1, U.S. Pat. Nos. 6,948,843 and 6,719,449 are incorporated by reference herein for details regarding the construction and operation of an acoustic transducer and its control.

The vessel 4 may have any suitable size or other arrangement, e.g., may be a glass tube, a plastic container, a well in a microtiter plate, a vial, or other, and may be supported at a location by a vessel holder 12. In this embodiment, the vessel 4 is a standard rimless 13×100 mm borosilicate glass test tube, but it should be understood that the vessel 4 may have any suitable shape, size, material, or other feature. For example, the vessel 4 may be a cylindrical tube with a flat bottom and a threaded top end to receive a cap, may include a cylindrical collar with a depending flexible bag-like portion to hold a sample, may be a single well in a multiwell plate, may be a cube-shaped vessel, or may be of any other suitable arrangement. The vessel 4 may be formed of glass, plastic, metal, composites, and/or any suitable combinations of materials, and formed by any suitable process, such as molding, machining, stamping, and/or a combination of processes.

The acoustic treatment system 100 may also include a coupling medium container 15 that is capable of holding a medium 16 (such as water or other liquid, gas, gel, solid, semi-solid, and/or a combination of such components) which transmits acoustic energy from the transducer 14 to the vessel 4. In some embodiments, the acoustic field may be controlled, the acoustic transducer 14 may be moved, and/or the vessel 4 may be moved (e.g., by way of moving a holder 12, such as a rack, tray, platform, etc., that supports the vessel 4) so that the sample is positioned in a desired location relative to the focal zone 17.

To control the acoustic transducer 14, the acoustic treatment system 100 may include a system control circuit 10 that controls various functions of the system 100 including operation of the acoustic transducer 14. For example, the system control circuit 10 may provide control signals to a load current control circuit, which controls a load current in a winding of a transformer. Based on the load current, the transformer may output a drive signal to a matching network, which is coupled to the acoustic transducer 14 and provides suitable signals for the transducer 14 to produce desired acoustic energy. As discussed in more detail below, the system control circuit 10 may control various other acoustic treatment system 100 functions, such as positioning of the vessel 4 and/or acoustic transducer 14, receiving operator input (such as commands for system operation), outputting information (e.g., to a visible display screen, indicator lights, sample treatment status information in electronic data form, and so on), and others.

In this illustrative embodiment, the sample 1 includes a solid material 2 and a liquid 3, e.g., 100 milligrams of a biological sample material in 1 milliliter of distilled water. Of course, those of skill in the art will appreciate that the sample 1 is not limited to a solid material 2 in a liquid 3, as the sample 1 may take any suitable form, such as a liquid only form, a solid only form, a mixture of liquid and solid as in this embodiment, a gel, a semi-solid, a gas, and/or combinations thereof.

An interface 5 separates the sample 1 from the headspace 6, which is shown to be a gaseous region immediately above the sample 1. For some power levels at the focal zone 17 and/or sample types or arrangements, acoustic energy suitable to cause mixing, e.g., lysing, extraction, permeabilizing, catalyzing, degrading, fluidization, heating, particle breakdown, shearing and/or disruption of molecular bonds in the sample 1 may also cause portions of the sample 1 (including solid material 2 and/or liquid material 3 of the sample 1) to be splashed or otherwise ejected from the interface 5. In some cases, the ejected sample 1 may return to the main volume of sample 1, but in other cases, the ejected sample 1 may adhere to the vessel 4 above the interface 5 or otherwise fail to return to the main sample 1. In either case, the ejected sample 1 may spend a reduced amount of time in the focal zone 17. By adding an energy director 8 (in this embodiment a relatively thin and long cylindrical or rod-shaped element) to the sample 1, the interaction between the acoustic energy at the focal zone 17 and the sample 1 may be modified so as to reduce splashing or other sample 1 ejection. The energy director 8 may function as a nucleation site for cavitation induced by the acoustic energy and cause shear forces created during cavitation bubble collapse to be directed to the surface of the energy director, instead of to portions of the sample. Thus, the sample may experience less shear stress and/or less dynamic stress during acoustic processing. The energy director may also (or alternately) function as a thermal energy emitter, if desired, e.g., the energy director may be heated by acoustic energy and release heat to surrounding sample material. Thus, heat gradients that may cause sample ejection may be reduced. In some embodiments, processes may benefit from application of both a combination of thermal and acoustic energy simultaneously, such as spore lysis, or other biological and/or medical related applications.

In some embodiments, the presence of the energy director 8 in the sample 1 may enable the use of higher power conditions than would otherwise be possible without an energy director 8. In one particular example employing an energy director 8, 100 microliters of fluid may be processed in a 300 microliter vessel without breaking the fluid surface layer at higher power acoustic dose settings than is possible without the energy director 8. As a result, the time that a sample 1 is exposed to an acoustic focal zone may be increased, as appropriately desired.

In some embodiments, an energy director 8 may be placed loosely in the sample 1 without being connected to the vessel 4, as shown in FIG. 1. In other embodiments, an energy director 8 may be attached to the vessel 4. For example, a rod-shaped energy director 8 like that in FIG. 1 may be attached to a cap 9 so that the energy director 8 depends from the cap 9 and extends into the sample 1 when the cap 9 is placed on the vessel 4. The connection of the energy director 8 to the cap 9 may help to transmit vibrational energy and/or thermal energy from the energy director 8 to the cap 9, e.g., which may be arranged to absorb the vibrational and/or thermal energy. In other arrangements, the energy director 8 may be attached more directly to the vessel 4, such as by welding, an adhesive, being molded integrally with the vessel 4, etc.

The energy director 8 may be a polymer, glass, metal or other suitable component, i.e., the choice of the material for the energy director 8 may be adjusted based on the desired end product and/or desired acoustic processing conditions for the sample 1. In some embodiments, an energy director 8 may be made of a quartz glass, borosilicate glass, alumina oxide, polypropylene (e.g., a rod-shaped element made by Bangs Labs, BB05N, 0.15-1.5 millimeters in diameter), stainless steel, PTFE, nylon, other suitable material, or a combination thereof. For isothermal acoustic cavitation, it may be desirable to have an energy director 8 include a material which does not retain thermal energy, such as glass or metal. Such an arrangement together with a sample vessel that readily dissipates heat (e.g., thin glass or thin polymer films such as Kapton®) may also be effective. In some DNA shearing applications, particularly when shearing relatively short DNA fragments (e.g., 3000 base pairs (3 kbp) and under) it has been found that the use of a hydrophilic material, such as glass or PTFE, may more efficiently direct acoustic energy to the sample to cause the desired shearing. It has also been found that shearing of longer DNA fragments (e.g., 10 k base pairs and up) can be effectively done using a hydrophobic material, such as some polymer materials. In one embodiment described below, the energy director made from a hydrophobic material for use in DNA shearing may include pores (e.g., similar to a sponge) of a suitable size, such as 100 microns, to cause desired shearing of DNA fragments.

An energy director can be of any suitable shape and size. As shown in FIG. 1, the energy director 8 has a rod shape. For example, a rod shaped energy director may have a length of about 10 millimeters and a width (or diameter) of about 1 millimeter. It should be understood that other shapes for the energy director 8 are possible, such a bead shape or plug shape as discussed further below. In some embodiments, bead energy directors may have a width (or diameter) of 0.025 millimeters, 0.1 millimeters, 0.5 millimeters or other suitable width. An energy director 8 having a bead form or any other appropriate shape may be buoyant or non-buoyant, and may function to interact with the interface 5 as well as function to control the acoustic energy/sample interaction.

Figure 2:
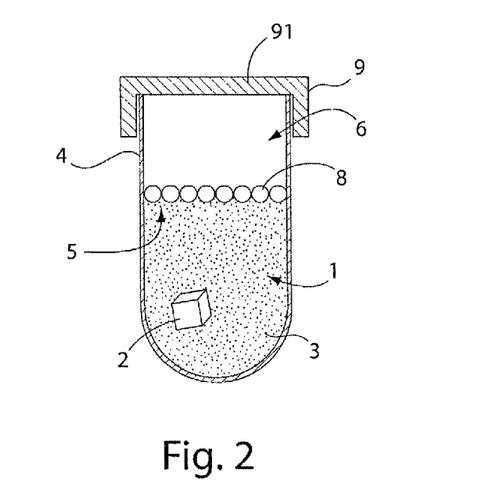
FIG. 2 is a section view of an embodiment of a sample in a vessel with an energy director in the form of one or more beads in accordance with aspects of the invention.

FIG. 2 shows an embodiment in which bead-shaped elements are used as energy directors 8. In this example, beads 8 may be buoyant so as to position themselves at the interface 5 and to help control interaction between acoustic energy used to treat the sample 1 and materials in the sample 1. A physical separation between the headspace 6 and the sample 1 may be maintained by the beads 8, even during a high power focused acoustic dose at higher levels than could be achieved without sample ejection. In addition, the beads 8 may provide energy director functions like that provided by the rod-shaped director 8 in FIG. 1. In some embodiments, after an acoustic process is complete, the sample 1 may be aspirated by a pipette that pushes the beads 8 to the side as the pipette tip opening is lowered below the surface of the sample fluid 3. Alternatively, other materials and configurations may be appropriately used for an energy director 8, such as a plug (e.g., made of Porex), a disc, wafer, or the like positioned at the interface 5.

Although in the embodiment shown in FIG. 2 a plurality of beads 8 are buoyant in the sample liquid 3 so that the beads 8 float at the interface 5, the beads 8 may be arranged in other ways. For example, the beads 8 may have physical properties such that when under a focused acoustic energy dose, the beads 8 are elevated upward to or near the fluid/air interface 5 by acoustic streaming, or are otherwise levitated under an applied focused acoustic field. Such control of interaction between acoustic energy and the sample may help prevent sample splashing or other ejection during acoustic processing. In other arrangements, the beads 8 may tend to avoid the interface 5 (e.g., sink toward the bottom of the vessel 4), or circulate more generally in the sample 1. The beads 8 may be made of a polymer material (e.g., polypropylene, Bangs Labs) and may be of different sizes, as discussed above. The vessel 4 in this embodiment may be annealed borosilicate glass (e.g., 6×32 mm) and include a septa 91 (e.g., having a split septum or other piercable portion) as part of the cap 9.

In another illustrative embodiment, an energy director may be arranged to enhance the fragmentation of DNA materials and/or otherwise influence the interaction between acoustic energy and the sample. In one specific example, a porous, generally hydrophobic plug of a polymer material (such as polypropylene or Porex material) may be positioned at or below the interface 5 in a 50-100 microliter vessel containing a sample 1 with DNA material. The plug may be attached to a cap 9, such as that shown in FIG. 2, and depend downwardly from the cap so that at least a portion of the plug is located at or below the interface 5. In one embodiment, the cap 9 is made from a solid piece of plug material and is arranged to not only cover the opening of the vessel 4, but also have a lower portion extend to the interface 5. The plug may have randomly or otherwise arranged pores (i.e., voids) that are exposed to the sample to assist in enhancing the shearing operation. The pores may range in size, for example, from 10-200 microns depending on the particular application. In one embodiment, the plug has pore sizes of about 100 microns with the pores randomly arranged. In this example, the starting DNA material may include DNA segments having a size of about 48.5 kbp. Acoustic treatment may be provided using a Covaris S2 AFA machine employing a 10% duty cycle, a 0.5 intensity level and 200 cycles per burst for approximately 4-8 minutes. After treatment, the majority (if not all) of the DNA fragments in the sample 1 are reduced in size to about 3 kbp. A fairly narrow range of final DNA fragment sizes may be produced, e.g., most of the DNA fragments may fall in a size range of about 1.5 kbp to about 5 kbp, and the range of DNA fragment sizes produced may be adjusted by adjusting characteristics of the energy director plug, including the material type, nominal pore size of the material and the hydrophobicity.

In another aspect of the invention, a processing volume or volume within which all or a portion of a sample is located for acoustic treatment, may be controlled in a vessel. For example, the gaseous headspace in a vessel may be reduced by positioning a wall, stop or other volume control member in the vessel so that the volume control member is located at or desirably near (e.g., above or below) a top surface of a sample in the vessel. The sample may be liquid, solid, a mixture of solid material in a liquid, or any other suitable arrangement. The vessel may take any suitable form as discussed above, such as a tube, well in a microtiter plate, a cube-shaped vessel, etc. In one embodiment, the volume control member may be suitably positioned with respect to the sample to reduce headspace without pressurizing the sample or other environment in the vessel. For example, the volume control member may allow pressure in the vessel to equilibrate with an atmospheric or ambient pressure outside the vessel. In one embodiment, a ratio of fluidic sample to headspace (e.g., gaseous space in the vessel between the volume control member and the sample) may be 5:1, 10:1, or greater.

In one illustrative embodiment, a volume control member may include a check-valve, a gas permeable membrane, filter, porous material, or orifice. For example, if the vessel in which a sample is placed has the shape of a tube, the volume control member may take the form of a plunger-like element that is inserted into the tube and suitably positioned in the tube so that the distal end of the plunger-like element is located at or near a top surface of the sample in the tube. A check-valve, gas permeable membrane, filter, orifice, bi-directional valve or other suitable component of the volume control member may allow gas to pass by the member during insertion into and/or removal from the tube.

In another aspect of the invention, a method for processing a sample includes providing a sample in a vessel, the vessel having a total volume, and the sample having a sample volume that is less than the total volume of the vessel. A processing volume may be defined in the vessel such that the processing volume is less than the total volume of the vessel and is a volume in which sample material to be subjected to acoustic energy is substantially confined. For example, if a 2 ml sample including liquid and solid material is placed in a 10 ml tube, a volume control member may be placed in the tube so as to define a processing volume that is less than 10 ml in which the sample is largely confined to during acoustic processing. The processing volume may be larger than the sample volume, e.g., 3 ml, such that there is a headspace present in the processing volume, or may be less than the sample volume, e.g., 1 ml. If the processing volume is less than the sample volume, some portions of the sample, e.g., liquid portions, may be permitted to exit the processing volume (e.g., by passing through a filter or other porous portion of the volume control member) while other portions of the sample (e.g., solid particles) may be kept in the processing volume. Once the processing volume is defined, the portion of the sample in the processing volume may be subjected to acoustic energy sufficient for gentle movement, lysing, extraction, permeabilizing, stirring, catalyzing, degrading, fluidization, heating, particle breakdown, disruption of molecular bonds, etc., in the sample. In one embodiment, the processing volume may be a volume defined by the volume control member itself, e.g., a portion of a filter that traps sample particles for acoustic processing, in addition to, or in place of, a portion of the vessel.

This aspect of the invention may provide advantages in some applications, such as when a relatively small amount of sample material is to be processed. That is, a small amount of sample material may in some cases require a relatively small processing volume be used during acoustic treatment, e.g., to ensure proper homogenization. However, if a volume control member is not used, providing a small volume for acoustic processing of the sample may require the use of a very small vessel. In reality, manually or otherwise placing a small sample in a small vessel may be, difficult, resulting in portions of the sample being lost or damaged. In accordance with this aspect of the invention, a relatively large vessel may be used to receive the sample, but the actual volume of the vessel in which the sample is located during acoustic processing may be reduced to a small size through the use of a volume control member. Thus, a relatively large vessel may be effectively converted to a small volume vessel for purposes of acoustic processing. Additionally, controlling interaction between a sample and acoustic energy directed to the sample may occur by minimizing the gaseous headspace above the sample in a processing vessel. As a result, a barrier prevents sample material from traveling significantly from the main sample volume and higher acoustic doses may be delivered to the sample. With higher acoustic doses, sample processing time may be reduced, further improving processing efficiency and target recovery.

Figure 3:
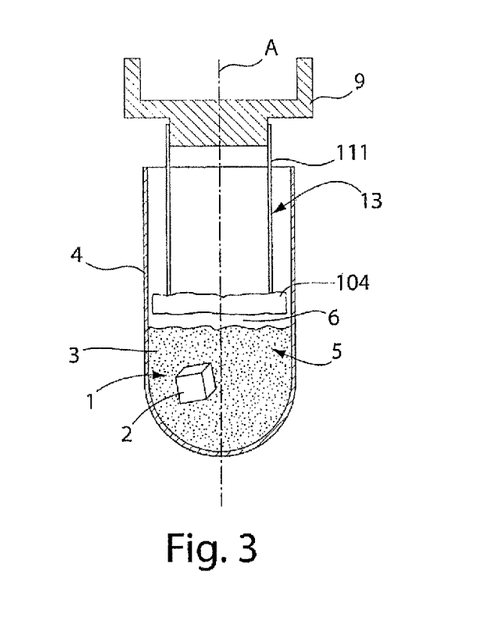
FIG. 3 is schematic of an embodiment showing use of a vessel with a sample and a volume control member in accordance with aspects of the invention.

As illustrated in FIG. 3, a volume control member 13 may be used to control a headspace 6 in the vessel 4, for example, to assist in preventing portions of the sample 1 from being splashed or ejected upwardly from an acoustic focal zone near the bottom of the vessel 4. In the embodiment depicted, the volume control member 13 includes a piston-like arrangement suitable for insertion into the open end of the vessel 4 and positioning of the distal end of the volume control member 13 near the sample 1. As shown, the volume control member 13 may include a number of features, such as a cylindrical tube 111 that carries an element 104 arranged to allow the member 13 to be moved along a longitudinal axis A in the vessel 4. In some cases, characteristics of a portion of the volume control member 13 that faces the sample 1 may affect acoustic processing results, e.g., a portion of the volume control element 13 may function as an energy director 8. Such characteristics of the volume control element 13 that may affect sample processing include, for example, choice of material, nominal pore size, and hydrophobicity. In this embodiment, the element 104 includes a piece of porous, hydrophobic material (e.g., a scaffold or matrix-type material) that may function, at least in part, as an energy director 8. This arrangement may be useful, e.g., in DNA shearing applications like that described above involving a plug-type energy director 8. The porous structure of the element 104 may also permit pressure in the vessel 4 at the sample 1 to equilibrate with pressure above the element 140. Further, if the element 104 is positioned below the interface 5, the element 104 may act as a type of filter, allowing portions of the sample 1 to pass, while maintaining larger solid material 2 below the element 104.

In some embodiments, the processing volume may include portions of the volume control element 13. For example, a portion of the sample (liquid and/or solid) may pass into or through a portion of an element 104 (such as the porous, hydrophobic element described above) and still be subjected to acoustic energy. Although the processing volume may extend through a portion of the volume control element, the volume control element may still serve to substantially confine the processing volume so that the sample may be suitably exposed to acoustic energy. As a result, the processing volume may be a volume defined by the volume control member itself; for example, a portion of a filter that traps sample particles for acoustic processing, in addition to, or in place of a portion of the vessel. Once the processing volume is defined, the portion of the sample in the processing volume may be subjected to acoustic energy sufficient for gentle movement, lysing, extraction, permeabilizing, stirring, catalyzing, degrading, fluidization, heating, particle breakdown, disruption of molecular bonds, or any other appropriate process, in the sample.

The embodiment shown in FIG. 3 also includes a cap 9 that may be used to close the proximal end of the tube 111 of the volume control member 13. By capping the proximal end of the volume control member 13, an operator may be able to prevent flow through or otherwise past the element 104 and/or prevent contamination of the sample 1 by the outside environment. Although not required, the cap 9 may be arranged as shown in FIG. 3 so as to allow capping of the vessel 4, if desired. In this illustrative embodiment, one end of the cap 9 may engage with the tube 111 of the volume control member 13 (shown in FIG. 3), whereas the opposite end of the cap 9 is enlarged so as to allow the cap 9 to be reversed from the position shown in FIG. 3 and placed on the end of the vessel 4.

Figure 4:
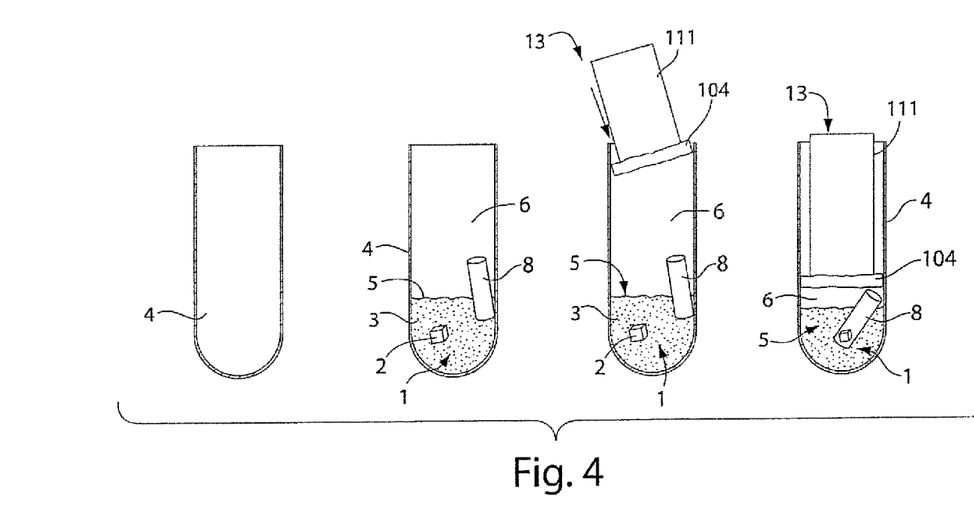
FIG. 4 shows steps in an illustrative method for providing a sample in a vessel with an energy director and a volume control member in accordance with aspects of the invention.

As shown in FIG. 4, when preparing a sample for processing by an acoustic processing device, a solid material 2 may be placed in the vessel 4 and liquid 3 or other material may be added to form the sample 1. Of course, placing a solid material 2 in the vessel 4 may occur subsequent to placing a liquid 3 in the vessel 4. As discussed above, the sample 1 may include one or more liquids, solids suspended or otherwise carried by a liquid, a gel, or any other suitable form. Regardless of the form of the sample 1, the sample may have an interface 5, which may be a gas/liquid interface, a gas/solid interface, or other suitable interface. An energy director 8 may also be optionally placed in the vessel 4 along with the sample 1, assisting in controlling the amount of energy exposed to the sample 1. To define the volume in which the sample 1 is to be processed, a volume control member 13 may be placed into the vessel 4, for example, as depicted in FIG. 3, by inserting the distal end of the tube 111 with the element 104 into the interior of the vessel 4 until the element 104 is suitably positioned near the sample interface 5 (i.e., above, at or below the interface 5).

The volume control member 13 may be positioned as desired, whether above the sample interface 5 as shown in FIG. 4, at the sample interface 5, or below the sample interface 5. In FIG. 4, no matter how large the headspace 6, being a gas-filled portion of the vessel adjacent the sample into which the sample may move, may be, the pressure Pi of headspace 6 is allowed to equilibrate with the pressure Po of the ambient environment. As shown, during acoustic processing, the headspace 6 may be decreased so as to minimize significant travel of sample material from the interface 5. If the element 104 is positioned at or below the sample interface 5, the headspace 6 may be effectively reduced to zero. In such a case, the material in the sample sought to be acoustically processed may be confined by the member 13 and not allowed to pass the member 13 as it is inserted into the vessel 4.

In some embodiments, the vessel 4 may contain a sample 1 that includes liquid 2 that nearly fills the vessel 4 and a solid material 3 suspended throughout the liquid. If the volume control member 13 is arranged like that in FIG. 3, the member 13 may serve to effectively filter the solid material 2 from the liquid 3 as the member 13 is advanced into the vessel 4 and allow liquid to pass and collect at the top of the vessel 4 while forcing the solid material 2 to collect near the bottom of the vessel 4. This may allow the solid material 2 to be confined to a smaller volume in the vessel, for example, near the bottom, and subjected to acoustic energy.

In another embodiment, the volume control member 13 may function to collect material for acoustic processing. For example, solid particles in the sample may be trapped in the element 104 in the embodiment of FIG. 3, and the trapped particles may be subjected to acoustic energy while contained in the element 104. Acoustic processing may break the particles into smaller pieces, allowing the material to be dissolved or otherwise be released from the element 104.

In contrast to the FIG. 3 embodiment described above, the element 104 may have a more impermeable arrangement, e.g., be formed of a flexible rubber or other suitable elastomer having a portion sized to be inserted in the distal end of the tube 111 so as to frictionally engage the element 104 with the tube 111. The element 104 may also include an annular sealing portion that contacts the inner wall of the vessel 4 and prevents the passage of liquid and/or gas at the contact point between the seal member 104 and the vessel 4, for example, similar to the manner in which a syringe plunger seals with a corresponding syringe barrel. In another illustrative embodiment, the member 13 may have the element 104 arranged so that a relatively small amount of liquid and/or gas may pass, for example, the annular seal member 104 may have a small cut or notch that prevents formation of a complete seal with the vessel wall. In another illustrative embodiment, the member 13 may have a one-way valve, for example, that allows gas and/or liquid to pass as the member 13 is inserted into or withdrawn from the vessel 4. In another embodiment, the member 13 may include a bi-directional valve that allows gas and/or liquid to pass as the member 13 is inserted into and withdrawn from the vessel 4. In various embodiments, the member 13 may include an orifice, serpentine passage, membrane or other structure that allows passage of gas and/or liquid in a controlled manner, yet prevents substantial portions of the sample material from exiting a desired area in the vessel 4. The volume control member 13 may be made of any suitable material or combination of materials, such as plastic, rubber, metal, glass, or the like. These materials may be selected based on any suitable criteria, such as chemical resistance, resiliency, stiffness, heat resistance, acoustic properties, etc. In one embodiment, the member 13 includes a PTFE material that is presented on a side near the sample, for example, to help prevent undesired adherence of the sample material to the member 13. In another embodiment, the element 104 having a flexible rubber portion may also include a porous portion like that described above, which may function as a type of filter.

Figure 5:
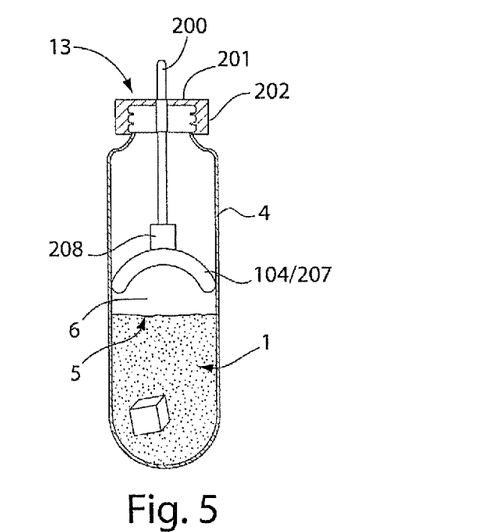
FIG. 5 is a section view of yet another embodiment of a sample in a vessel with a volume control member in accordance with aspects of the invention.

FIG. 5 shows a illustrative embodiment of a sample vessel and volume control member that includes a generally impermeable material. In this embodiment, a cylindrical vessel 4 (e.g., 13×65 mm borosilicate glass), which includes a matched screw-threaded cap 202 and septa 201, is shown with a volume control member 13 in the form of an adjustable piston assembly, including a rod 200, a couplant 208 to affix the tip with the rod and an element 104 in the form of a piston tip 207. The rod 200 may be formed by any suitable manner, such as injection molding. Any suitable couplant 208 may be used, such as a crimped metal or extruded plastic ring. The piston tip 207 may be formed from any appropriate material, such as silicone, rubber, plastic, or the like. The rod 200 is inserted through a slit or other opening in the septa 201, allowing the volume control member 13 to be moved vertically relative to the septa 201. In this embodiment, the piston tip 207 is of greater diameter than the internal diameter of the cylindrical vessel 4, allowing for an interference fit between the piston tip 207 and the vessel 4.

For example, an interference fit shown in FIG. 5 may be formed by the piston tip 207 having a 1.0 millimeter greater diameter than the internal diameter of 10 millimeters of the vessel 4. The degree of interference may be dependent on several factors, including the durometer, thickness, and/or material of the piston tip 207. In one embodiment, the tip 207 is preferably made of a polymeric material. The interference fit may allow a piston tip 207 to be both inserted into and removed from a vessel which has a constricting neck. During sample loading, the flexible tip 207 may take a convex shape on its bottom surface relative to the sample at or near the interface 5 and allow pressure in the vessel 4 to be vented close to or at the ambient atmospheric pressure. Venting may occur, for example, in a space between the piston tip 207 and the vessel wall. If the piston rod 200 is pulled in the opposite direction away from the sample a slight distance, the piston tip 207 may invert, causing the convex shape assumed during insertion to become concave, as shown in FIG. 5. A concave surface of the piston tip 207 facing the sample at or near the interface 5 may help prevent sample material from being splashed upward out of the focal zone during a high power dose and aid the return of any ejected sample material back to the main sample. In addition, a concave shape of the piston tip 207 may minimize sharp edges (as may occur with a convex shape) to aid in the return of the sample to the main sample.

In accordance with another aspect of the invention, a vessel may be associated with a holder that helps support the vessel during acoustic treatment. A holder 12 may take any suitable arrangement, such as a ring-shaped element 12 that is fixed relative to the vessel 4, as shown in FIG. 1. The holder 12 may be permanently fixed to the vessel 4, e.g., molded integrally with the vessel 4, attached to the vessel 4 by an adhesive, a fastener, welding, etc., or may be removably attached to the vessel. For example, in some embodiments, the vessel holder 12 may include a ring member like that shown in FIG. 1 and one or more O-rings (not shown) or other friction-enhancing elements that are positioned between the ring member and the vessel 4 to provide a tight friction fit between the vessel 4 and the holder 12. Such an arrangement may be useful when interchanging vessels 4 on a single holder 12 and/or adjusting the position of the vessel 4 relative to the holder 12.

Although a vessel holder 12 is not necessarily required, the vessel holder 12 may serve to interface with the acoustic processing device so that the vessel 4 and the sample in the vessel is positioned in a known location relative to an acoustic field, for example, at least partially within a focal zone of acoustic energy. Such an arrangement, coupled with the use of a volume control member 13, may allow an operator to closely define the location in which the sample is positioned during acoustic processing.

Figure 6:
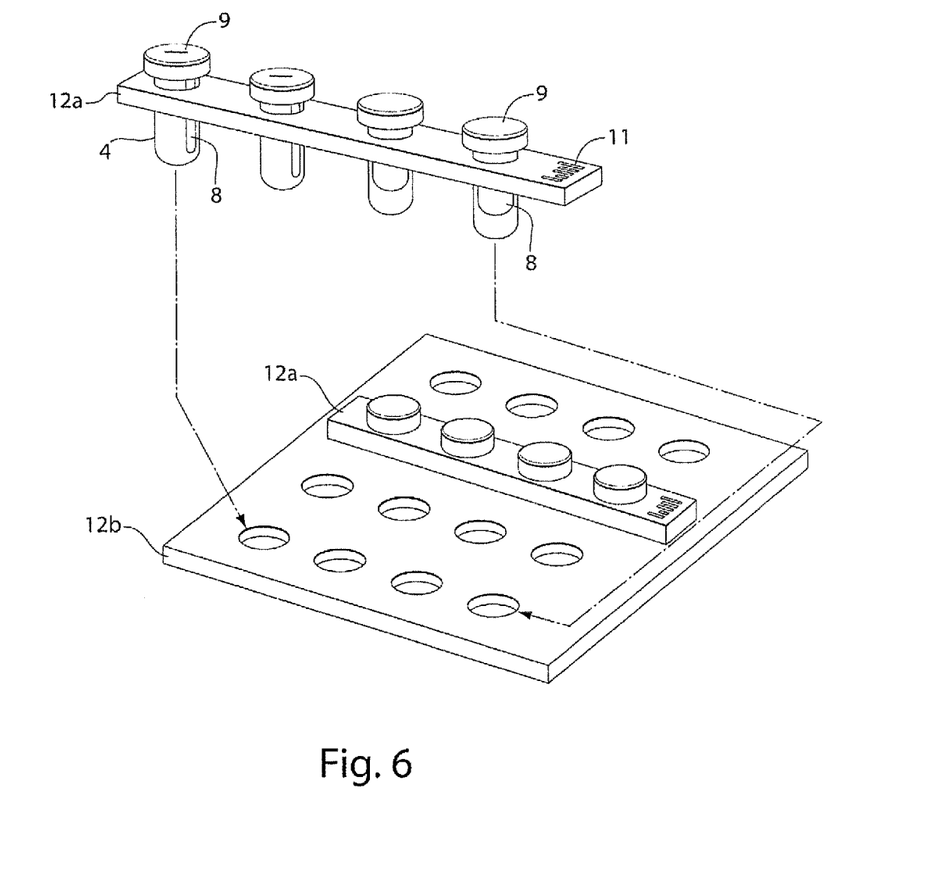
FIG. 6 shows an embodiment in which a holder includes a support that holds a subset of vessels and a rack arranged to receive a plurality of supports and associated vessels.

Although in the FIG. 1 embodiment the holder 12 is located near a middle of the vessel 4, the holder 12 may be positioned in any suitable manner relative to the vessel 4, such as near the bottom or top of the vessel, extending from one side of the vessel, and/or any other appropriate position. Also, the holder 12 is not limited to a device like that shown in FIG. 1, and instead may include a rack, slot, tray, gripper element, clamp, box or any other suitable arrangement for holding the vessel in a desired location. For example, FIG. 6 shows an arrangement in which the holder 12 includes one or more multi-vessel supports 12a and a rack 12b. Each support 12a may hold a plurality of vessels 4, e.g., in a linear array as shown. Although in this embodiment the support 12a is arranged to hold four vessels 4, any suitable number of vessels may be associated with a support 12a, such as eight tubes in a linear array. Each support 12a may include an identifier 11, such as a barcode, RFID chip, or other component that may be read so as to identify the support 12a and/or vessels 4 associated with the support 12a. The vessels 4 may be arranged in any desired way, such as having a rod-shaped energy director 8 that depends from a cap 9 having a split septum (to allow aspiration/dispense of sample in the vessel 4 without removing the cap 9) as shown on the left end of the support 12a above the rack 12b, or an energy director 8 in the form of an end of a cap 9 that depends down into the vessel 4 to interact with the sample as shown on the right end of the support 12a. The vessels 4 may be held in place by an interference fit with holes formed in the support 12a, or may otherwise be associated with the support 12a. In this embodiment, the vessels 4 depend below the support 12a so that lower ends of the vessels 4 may be received in corresponding holes in the rack 12b. The rack 12b may have any suitable arrangement, but in this embodiment includes a plate with holes formed in an arrangement to receive multiple supports 12a and associated vessels 4. The rack 12b may make it easier to physically manipulate or otherwise handle multiple vessels 4, e.g., in an automated processing environment in which one or more robotic devices manipulate vessels for acoustic or other processing. The rack 12b may also include an identifier (not shown) so that the rack 12b and/or supports 12a on the rack 12b can be identified in a automated way, e.g., by a laser scanner, optical camera, RFID tag reader or other arrangement.

Figure 7:
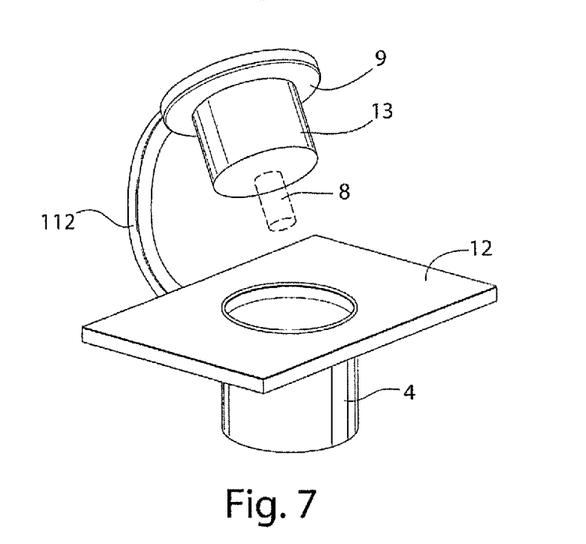
FIG. 7 is a perspective view of a further embodiment of a vessel and a volume control member in accordance with aspects of the invention.

It should be understood that in one embodiment, the vessel 4, vessel holder 12, energy director 8 and/or volume control member 13 may be separately formed parts that are later associated together, whereas in another embodiment, the vessel 4, vessel holder 12, energy director a and/or volume control member 13 may be unitarily formed, e.g., molded together as a single piece. For example, FIG. 7 shows another illustrative embodiment of a sample vessel in which multiple components are formed as a single piece. In this embodiment, the vessel 4 and the holder 12 are molded as a single unitary piece with the vessel 4 depending from the holder 12. Although in this embodiment, the vessel 4 has a cylindrical shape and the holder 12 has a rectangular shape, it should be understood that the vessel 4 and the holder 12 may take any suitable configuration. Thus, the vessel 4 may define a cylindrical, conical, frustoconical, cubic or other box-like, spherical, mushroom-like or other suitably shaped volume for receiving the sample. The holder 12 may have an elliptical, circular, rectangular, triangular, or other shape, at least as viewed from the top. In a 3-dimensional sense, the holder 12 may take a conical, cylindrical, frustoconical, cubic or any other shape or combination of shapes. Of course, the holder 12 or the vessel 4 may have an irregular shape of any suitable kind.

Also in this embodiment, the volume control member 13 is attached to a cap 9, with a cylindrical portion depending from a circular cap 9. As in the embodiments described above, the member 13 may include a valve structure, filter, porous material, orifice, sponge, or other arrangement to allow selective passage of gas. In one embodiment, the cylindrical portion may have a slot, groove, flat or other feature on its sidewall that prevents the formation of a complete seal with the vessel 4, thereby allowing gas to pass. In another embodiment, the cylindrical portion may be sized smaller than the vessel inner wall to prevent a complete seal from being formed between the member 13 and the vessel 4. Although in this embodiment the member 13 may be separate from the vessel 4 and holder 12, it is possible to have the member 13 attached to the vessel 4 or holder 12, for example, by a hinge, tether 112, or other feature. For example, it is possible to mold the vessel 4, holder 12, and the member 13 as a single unitary member with a tether 112 connecting the member 13 to the holder 12 as shown in FIG. 7. Other arrangements are possible, e.g., where an energy director 8 is provided in place of the volume control member 13, or where an energy director 8 depends from the volume control member 13 for positioning in the sample 1.

A few examples regarding use of a volume control member arranged like that in FIG. 3 are described below.

EXAMPLE ONE

Tissue samples, approximately 500 milligrams of frozen chicken breast tissue (solid piece), were stored at −70 degrees C. and inserted into a test tube vessel. 1.5 milliliters of distilled water (prechilled to <10 degrees C.) was added to the tube. A volume control member 13 with a porous p-propylene material functioning as a vent or filter was inserted into the tube and the member 13 moved into position just above the fluid level leaving approximately 0.5 milliliters of gas/vapor headspace. The tube was inserted into a Covaris S2 system for 30 seconds at duty cycle 20%, intensity 10, and 200 cycles/burst. The member 13 kept the sample in the focal zone, eliminated the need for a degassing step, and accelerated homogenization of the tissue sample. Following homogenization, the member 13 was removed and the vessel with the sample was capped.

EXAMPLE TWO

As in Example one above, however, after the Covaris S2 acoustic process, 4 milliliters of MeOH was added to the volume control member's 13 inner compartment (inside the cylindrical tube 111) and the member 13 was moved to enable the solvent to pass through the member 13 and into the homogenate. The homogenate plus MeOH was then treated for less than 10 seconds to mix and the member 13 was pressed to allow the extracted material to pass through the porous element 104, while leaving the particulate and material at the bottom of the vessel 4.

EXAMPLE THREE

Shearing of a 3 kb target fragment of DNA was performed using a Covaris S2 system for a single sample and a Covaris E210 system for multiple samples. A polypropylene tube was used as a vessel and was attached with a snap cap. The duty cycle used was 10% at an intensity of 0.1. There were 1,000 cycles per burst for a time period of 420 seconds. The temperature of the bath was 20 C. A frequency sweeping power mode was set under a continuous degassing mode. The volume of the vessel was 95 microliters, the buffer used being tris EDTA at pH 8.0 (no glycerol). A plug-type energy director was used. Less than 1.5 micrograms of DNA were used. The starting material including DNA fragments with lengths greater than 48 kbp.

The size and nature of the starting material (e.g., PCR products, 2 kb, 48 kb, mammalian genomic) affected the time dosages required to achieve desired shearing results (e.g., 4 minutes, 6 minutes, 8 minutes, etc.). Starting material greater than 3 micrograms was shown to require lower viscosity conditions of the sample prior to fragmentation. If the viscosity was not reduced, particularly for fragments greater than 500 bp, variation between samples were observed.

To reduce viscosity effects with long fragments, relatively short doses (e.g., 10% duty cycle, level 0.5 intensity, 200 cycles per burst) were helpful prior to the desired fragmentation dose. A duty cycle of 10%, level 0.5 intensity, and 1,000 cycles per burst for 3 seconds was also used for a short burst. For example, 5 micrograms per 100 microliters has been used with both linearized lambda and mammalian genomic DNA with short doses of 3 seconds. Different samples have required adjustment of time (e.g., 2, 3, 4, 5 seconds, etc.). The sample was slightly fragmented to allow flow of the fragments into the active acoustic zone, which is the bottom surface of the plug.

The vessel had a volume range of 50 to 100 microliters for DNA shearing and was designed for use at an intensity level of 5 or less. Upon volume reduction, duty cycle was reduced to less than 10%.

Generally, larger length starting materials (e.g., 100 kb) and larger masses (e.g., 5 micrograms) have required longer time doses. Circular DNA has required a short, high dose followed by a long, low dose to shear to a desired fragment size.

As described above, the system control circuit 10 may include any suitable components to perform desired control, communication and/or other functions. For example, the system control circuit 10 may include one or more general purpose computers, a network of computers, one or more microprocessors, etc. for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the load current control circuit as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the medium 16, a video camera or other imaging device to capture and analyze image information regarding the vessel 4 or other components, position sensors to indicate positions of the acoustic transducer 14 and/or the vessel 4, and so on), user data input devices (such as buttons, dials, knobs, a keyboard, a touch screen or other), information display devices (such as an LCD display, indicator lights, a printer, etc.), and/or other components for providing desired input/output and control functions.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

What is claimed is:
1. An acoustic treatment device, comprising:
a vessel arranged to hold a sample that includes a liquid, the vessel capable of holding a sample volume of about 300 microliters or less; and a cap constructed and arranged to engage with the vessel and cover an opening of the vessel, the cap including a split septum; and an energy director including a rod attached to and depending from the cap and configured to be positioned in a portion of the sample when the cap is engaged with the opening, the energy director having a hydrophobic or hydrophilic surface with crevices, wherein the surface with crevices is arranged to be located in the sample to disrupt material of the sample on or near the surface with crevices by controlling interaction between acoustic energy having a frequency of between about 100 kilohertz and about 100 megahertz and a focal zone with a width of less than about 2 centimeters and the sample when the acoustic energy is emitted remotely from the vessel and applied to the vessel.

2. The device of claim 1, wherein the energy director is made of a hydrophilic material and the vessel is made of a hydrophilic material, and wherein the vessel and energy director are arranged to enhance shearing of DNA in the sample having a base pair length of 3000 or less caused by the acoustic energy.

3. The device of claim 1, wherein the energy director is made of a hydrophobic material and the vessel is made of a hydrophobic material, and wherein the vessel and energy director are arranged to enhance shearing of DNA in the sample having a base pair length of 3000 or more caused by the acoustic energy.

4. The device of claim 1, further comprising an acoustic energy source for providing the acoustic energy having the focal zone to the sample while the sample is in the vessel and separated from the acoustic energy source; and a vessel holder arranged to support the vessel, the vessel holder adapted to position the vessel at a location at least partially in the focal zone of the acoustic energy.

5. The device of claim 1, wherein the energy director is configured to control a headspace of the sample in the vessel.

6. The device of claim 5, wherein the cap and the energy director are configured to reduce splashing in the headspace of the sample in the vessel.

7. The device of claim 1, wherein the energy director is adapted to increase mixing of the sample that would otherwise be less in the absence of the energy director.

8. The device of claim 1, wherein the septum is adapted to move relative to the vessel resulting in adjustment of a headspace of the sample in the vessel.

9. The device of claim 1, wherein the septum provides a seal at the opening of the vessel.

10. The device of claim 1, wherein the crevices are naturally occurring defects of the hydrophobic or hydrophilic surface.

11. The device of claim 1, wherein the crevices are artificially occurring from scratching, etching, grinding, engraving, milling, drilling, sand blasting, ion-beam processing, molding, pressing, hot stamping, microlithography, micromachining or microfabrication.

12. The device of claim 1, wherein the crevices lower a cavitation threshold of the sample on the surface of the energy director.

13. The device of claim 12, wherein the crevices promote cavitation in the sample that increases mixing of the sample that would otherwise be less in the absence of the cavitation in the sample.

14. The device of claim 1, wherein the energy director includes at least one element that is rod-shaped, plug-shaped, bead-shaped or irregularly shaped.

15. The device of claim 1, wherein the energy director, the cap and the vessel are constructed and arranged to enhance the shearing of nucleic acid in the sample to 3000 base pairs or less.

16. The device of claim 6, wherein the reduction of splashing at the headspace of the sample in the vessel enhances a duration in which the sample is exposed to the focal zone of the acoustic energy.

17. The device of claim 1, wherein the energy director is formed unitarily with the cap.

* * * * *